US010289753B2

(12) United States Patent
Snaterse et al.

(10) Patent No.: US 10,289,753 B2
(45) Date of Patent: May 14, 2019

(54) METHODS AND SYSTEMS FOR GUIDANCE OF HUMAN LOCOMOTION

(75) Inventors: Mark Snaterse, Port Moody (CA); Sung Jae Chang, Toronto (CA); James Maxwell Donelan, North Vancouver (CA)

(73) Assignee: Simon Fraser University, Burnaby (CA)

( * ) Notice: Subject to any disclaimer, the term of this patent is extended or adjusted under 35 U.S.C. 154(b) by 1244 days.

(21) Appl. No.: 13/808,886

(22) PCT Filed: Jul. 7, 2011

(86) PCT No.: PCT/CA2011/050417
§ 371 (c)(1),
(2), (4) Date: Jan. 7, 2013

(87) PCT Pub. No.: WO2012/003588
PCT Pub. Date: Jan. 12, 2012

(65) Prior Publication Data
US 2013/0110266 A1    May 2, 2013

Related U.S. Application Data

(60) Provisional application No. 61/362,170, filed on Jul. 7, 2010.

(51) Int. Cl.
*G06F 17/40* (2006.01)
*A61B 5/11* (2006.01)
(Continued)

(52) U.S. Cl.
CPC ............ *G06F 17/40* (2013.01); *A61B 5/1112* (2013.01); *A63B 69/0028* (2013.01);
(Continued)

(58) Field of Classification Search
CPC ....... G05B 11/42; G05B 13/044; G06F 17/40; A63B 69/0028; A63B 71/0686;
(Continued)

(56) References Cited

U.S. PATENT DOCUMENTS 5,455,495 A     10/1995   Bec
5,898,340 A *   4/1999    Chatterjee ............ H03F 3/2171
                                                    330/251
(Continued)

FOREIGN PATENT DOCUMENTS

GB         2432282        5/2007

OTHER PUBLICATIONS

Salo, A.I.T. et al., "Elite sprinting: are athletes individually step-frequency or step-length reliant?", Medicine & Science in Sports & Exercise, Jun. 2011, pp. 1055-1062.
(Continued)

*Primary Examiner* — Charles R Kasenge
(74) *Attorney, Agent, or Firm* — Todd A. Rattray; Oyen Wiggs Green & Mutala LLP

(57) ABSTRACT

A method is provided for guiding locomotion speed in a human or other animal subject. The method comprises: estimating the subject's actual locomotion speed using one or more sensors to thereby obtain a measured speed; determining an error comprising a difference between a desired speed and the measured speed; and outputting, to the subject, a stimulus frequency signal wherein the stimulus frequency signal is based on the error in such a manner that when the subject ambulates in a manner that matches a frequency of the stimulus frequency signal, the subject's actual speed controllably tracks the desired speed.

59 Claims, 7 Drawing Sheets

(51) Int. Cl.
  *A63B 69/00* (2006.01)
  *A63B 71/06* (2006.01)
  *G05B 11/42* (2006.01)
  *A61B 5/024* (2006.01)
  *G01S 19/19* (2010.01)
  *A61B 5/00* (2006.01)

(52) U.S. Cl.
  CPC .......... *A63B 71/0686* (2013.01); *G05B 11/42* (2013.01); *A61B 5/024* (2013.01); *A61B 5/1123* (2013.01); *A61B 5/6829* (2013.01); *A61B 2505/09* (2013.01); *A63B 2071/0625* (2013.01); *A63B 2071/0627* (2013.01); *A63B 2071/0655* (2013.01); *A63B 2208/14* (2013.01); *A63B 2220/10* (2013.01); *A63B 2220/12* (2013.01); *A63B 2220/30* (2013.01); *A63B 2220/836* (2013.01); *A63B 2225/20* (2013.01); *A63B 2225/50* (2013.01); *A63B 2230/062* (2013.01); *A63B 2230/207* (2013.01); *G01S 19/19* (2013.01)

(58) Field of Classification Search
  CPC ........ A63B 2071/0655; A63B 2225/50; A63B 2220/836; A63B 2220/30; A63B 2220/10; A63B 2208/14; A63B 2225/20; A63B 2071/0627; A63B 2071/0625; A63B 2230/062; A63B 2230/207; A63B 2220/12; A61B 5/1112; A61B 2505/09; A61B 5/6829; A61B 5/024; A61B 5/1123
  See application file for complete search history.

(56) References Cited

U.S. PATENT DOCUMENTS

| | | | |
|---|---|---|---|
| 5,921,890 A | 7/1999 | Miley | |
| 6,513,381 B2 | 2/2003 | Fyfe et al. | |
| 7,683,252 B2* | 3/2010 | Oliver | A61B 5/02438 84/612 |
| 7,728,214 B2* | 6/2010 | Oliver | A61B 5/0006 84/612 |
| 7,745,716 B1* | 6/2010 | Murphy | A63B 71/0686 84/612 |
| 7,771,320 B2* | 8/2010 | Riley | A63B 24/0006 482/9 |
| 7,825,319 B2* | 11/2010 | Turner | G10H 1/40 482/3 |
| 7,841,965 B2* | 11/2010 | Shirai | A63B 71/0686 482/8 |
| 7,927,253 B2* | 4/2011 | Vincent | A63B 24/0021 482/9 |
| 8,112,251 B2* | 2/2012 | Case, Jr. | A63B 24/00 702/182 |
| 8,702,430 B2* | 4/2014 | Dibenedetto | G16H 15/00 434/247 |
| 2004/0186390 A1* | 9/2004 | Ross | A61B 5/083 600/532 |
| 2006/0030458 A1 | 2/2006 | Heywood | |
| 2006/0111621 A1* | 5/2006 | Coppi | A61B 5/222 600/300 |
| 2006/0136173 A1* | 6/2006 | Case, Jr. | A63B 24/00 702/182 |
| 2006/0253210 A1 | 11/2006 | Rosenberg | |
| 2007/0027000 A1* | 2/2007 | Shirai | A63B 71/0686 482/8 |
| 2007/0074617 A1 | 4/2007 | Vergo | |
| 2007/0079691 A1* | 4/2007 | Turner | G10H 1/40 84/612 |
| 2007/0113725 A1* | 5/2007 | Oliver | A61B 5/02438 84/612 |
| 2007/0113726 A1* | 5/2007 | Oliver | A61B 5/0006 84/615 |
| 2007/0118043 A1* | 5/2007 | Oliver | A61B 5/0245 600/519 |
| 2007/0287596 A1* | 12/2007 | Case, Jr. | A63B 24/00 482/8 |
| 2008/0004160 A1* | 1/2008 | Kennard | A63B 71/0686 482/2 |
| 2008/0013651 A1* | 1/2008 | Taya | H04L 27/0008 375/344 |
| 2008/0096726 A1* | 4/2008 | Riley | A63B 24/0006 482/8 |
| 2008/0097633 A1* | 4/2008 | Jochelson | A63B 71/0686 700/94 |
| 2008/0109158 A1* | 5/2008 | Huhtala | A63B 24/0021 701/439 |
| 2008/0153671 A1* | 6/2008 | Ogg | A63B 71/0686 482/3 |
| 2008/0188354 A1* | 8/2008 | Pauws | A63B 71/0686 482/8 |
| 2008/0200312 A1* | 8/2008 | Tagliabue | G01C 22/006 482/9 |
| 2008/0214358 A1 | 9/2008 | Ogg et al. | |
| 2008/0218310 A1* | 9/2008 | Alten | A43B 5/00 340/5.8 |
| 2008/0236370 A1 | 10/2008 | Sasaki et al. | |
| 2008/0254946 A1* | 10/2008 | Pauws | A63B 71/0686 482/8 |
| 2008/0306619 A1* | 12/2008 | Cerra | G11B 27/10 700/94 |
| 2009/0044687 A1* | 2/2009 | Sorber | A63B 71/0622 84/609 |
| 2009/0047645 A1* | 2/2009 | Dibenedetto | G16H 15/00 434/258 |
| 2009/0048044 A1* | 2/2009 | Oleson | A63B 24/0062 473/570 |
| 2009/0048070 A1* | 2/2009 | Vincent | A63B 24/0021 482/8 |
| 2009/0131224 A1 | 5/2009 | Yuen | |
| 2009/0198386 A1* | 8/2009 | Kim | H02P 9/102 700/298 |
| 2009/0233770 A1* | 9/2009 | Vincent | A63B 24/0021 482/8 |
| 2009/0319230 A1* | 12/2009 | Case, Jr. | A63B 24/00 702/182 |
| 2010/0210421 A1* | 8/2010 | Case, Jr. | A63B 24/00 482/8 |
| 2010/0210975 A1 | 8/2010 | Anthony, III et al. | |
| 2010/0279825 A1* | 11/2010 | Riley | A63B 24/0006 482/8 |
| 2011/0166488 A1* | 7/2011 | Miyake | A61B 5/112 601/34 |
| 2014/0050335 A1* | 2/2014 | Moronvalle | H03F 3/68 381/120 |

OTHER PUBLICATIONS

Snaterse, M. et al., "Cruise control for runners", Simon Faser University public affairs and media relations, published online Feb. 11, 2011 (Nov. 2, 2011) http://www.sfu.ca/archive-pamr/media_releases/media_releases_archives/cruise-control-for-runners.html.
Apple Nike + iPod, Rock and Run, http:www.apple.com/ipod/nike/run.html, accessed Jul. 5, 2010.
Garmin Forerunner, http://buy.garmin.com/shop/shop.do?pID=349&ra=true, accessed Jul. 5, 2010.
Kineteks Tractivity, http:www.kinetekscorp.com/Products/tractivity.html, available Sep. 2008.
Dr. Nuria Oliver Triple Beat System, http://nuriaoliver.com/TripleBeat/TripleBeat.htm, available Jun. 25, 2010.
Polar Get Active, www.polarusa.com/us-en/products/get_active, available Jun. 30, 2011.
KulzerTec GBK-Pacer, http://www.kulzertec.com/Paperl.html, accessed Jul. 5, 2010.
Schachner, Adena et al., "Spontaneous Motor Entrainment to Music in Multiple Vocal Mimicking Species", Current Biology 19: 831-836, May 26, 2009.

(56) References Cited

OTHER PUBLICATIONS

SpeedMax White Paper, Dynastream Innovations Inc., www.dynastream.com, accessed Jul. 5, 2010.
Styns, Frederik et al. "Walking on Music", ScienceDirect, Human Movement Science 26 (2007) 769-785, available online at www.sciencedirect.com.
Wired Magazine, "The Nike Experiment: How the Shoe Giant Unleashed the Power of Personal Metrics", http://www.wired.com/medtech/health/magazine/17-07/lnp_nike, Jun. 22, 2009.
Yamaha BodiBeat, http://www.yamaha.com/bodibeat/, available Jun. 25, 2010.
Polar S3 Stride Sensor W.I.N.D., www.polarca.com/ca-en/products/accessories/s3_Stride_Sensor_WIND, available Sep. 2008.
Polar S3 Stride Sensor W.I.N.D., http://www.pursuit-performance.com.au/polar/html/local/accessories/S3-Stride-Sensor.html, accessed Jul. 5, 2010.
Nike Running—SportBand with User's Guide, http://www.nikerunning.nike.com/nikeos/p/nikeplus/en_EMEA/sportband, accessed Jul. 5, 2010.
Minetti, A.E. (1998), "A Model equation for the prediction of mechanical internal work of terrestrial locomotion", Journal of Biomechanics, 31: 463-468.
Gutmann A.K., B. Jacobi, M.T. Butcher & J.E.A. Bertram (2006), "Constrained optimization in human running", The Journal of Experimental Biology, 209: 622-632.
Green JM, Sapp AL, Pritchett RC & Bishop PA (2010), "Pacing accuracy in collegiate and recreational runners", European Journal of Applied Physiology, 108: 567-572.
Hermansen L. & Saltin B (1969) "Oxygen uptake during maximal treadmill and bicycle exercise", Journal of Applied Physiology, 26: 31-37.
Garmin Owner's Manual—Forerunner 205/305, dated Jul. 2008.
Polar s3 Stride Sensor W.I.N.D. User Manual, dated 2009.
Mio Sport Instruction Manual, "EKG-Accurate Heart Rate with Maximum Heart Rate Indicator + Chronograph Timer", available Jun. 30, 2011.

* cited by examiner

METHODS AND SYSTEMS FOR GUIDANCE OF HUMAN LOCOMOTION

RELATED APPLICATIONS

This application claims the benefit of the priority of U.S. application No. 61/362170 filed 7 Jul. 2010 which is hereby incorporated herein by reference. For the purposes of the United States, this application claims the benefit of U.S. application No. 61/362170 filed 7 Jul. 2010 under 35 USC § 199(e).

TECHNICAL FIELD

This invention relates to the automatic control of human locomotion (e.g. running and/or walking). Some embodiments provide methods and systems for automatic control of human locomotive speed, position and/or intensity.

BACKGROUND

There is a general desire to describe and/or control various means of human locomotion. Such description and/or control can assist with navigation, predicting arrival times and the like. For example, the description of the speed of an automobile (e.g. provided by a speedometer) may be used to predict how far the automobile can travel in a particular length of time and/or when the automobile will arrive at a particular destination. Speed control of the automobile (e.g. provided by a cruise control system) can be used to achieve target arrival times, target speeds and the like.

There is a similar desire to describe and/or control human locomotion (e.g. locomotion, such as running, walking and/or the like).

Like the case of the exemplary automobile discussed above, such control can assist with achieving target navigation parameters, such as arrival times and the like. By way of non-limiting example, description and control of human locomotion can also have application to training (e.g. for athletes, recreational runners, soldiers and the like). Many runners, ranging from world class athletes to recreational runners, set objectives (goals) to cover a given distance in a certain amount of time. To achieve such objectives, such runners have to run the distance at a particular speed or with a particular speed profile.

Various systems and techniques are known in the prior art to estimate running/walking speed and/or position. Such prior art systems include:

The "Nike+"™ sportsband developed by Nike, Inc and the "Rock and Run"™ system developed by Apple Inc. in conjunction with Nike, Inc. use an in-shoe sensor and a handheld or band-mounted user interface to estimate time, distance and speed and to provide such information to the shoe wearer—(see http://nikerunning.nike.com/nikeos/p/nikeplus/en_EMEA/sportband and http://www.apple.com/ipod/nike/run.html).

The "Forerunner"™ series of wrist-worn devices sold by Garmin Ltd. which use global positioning system (GPS) technology to estimate position, speed and time and to provide such information to the user—(See https://buy.garmin.com/shop/shop.do?cID=141&fKeys=FILTER_SERIES_FORERUNNER).

The "Polar S3 Stride Sensor W.I.N.D."™ sensor sold by Polar Electro Oy which mounts to the user's shoe, measures the acceleration of a user's foot and uses this acceleration information to estimate ground speed and/or distance—(http://www.polarusa.com/us-en/products/accessories/s3_Stride_Sensor_WIND).

The "Speedmax"™ technology developed by Dynastream Innovations Inc. which uses inertial sensors to detect running/walking speed and distance.

Other than for providing the user with information about their speed, however, these systems and techniques do not appear to permit automatic control of human running/walking speed and/or position. Using such systems, a user would have to repetitively monitor the user interface (or repetitively receive output from an output device (e.g. headphones)) and then the user would have to determine on their own whether they were meeting their speed objective. Based on their own consideration of whether they were meeting their speed objective, the user would then have to adjust their speed on their own and then recheck the user interface at a later time to determine if their new speed meets the speed objective. For most humans, this speed adjustment is difficult to perform accurately. No information is provided to the user between the time that the user first checks the user interface and the time that the user subsequently rechecks the user interface at the later time. These systems are analogous to the speedometer of an automobile, wherein speed information is provided to the driver, but the driver adjusts the speed on their own (i.e. without automatic cruise control). Such systems do not provide automatic speed control of locomotion in a manner that is analogous to cruise control in an automobile.

There is a desire for systems which help a subject to automatically control a speed and/or position of their human locomotion (e.g. locomotion such as running and/or walking).

In addition to or in the alternative to controlling locomotive speed and/or position, there is a general desire to control locomotion intensity. Locomotive intensity is usually estimated based on one or more measurable or estimatable or measurable intensity indicators. Such intensity indicators include, by way of non-limiting example, hear rate, metabolic rate, oxygen consumption, perceived exertion, mechanical power and/or the like.

Various systems and techniques are known for estimating hear rate. Such systems include:

Strapped heart rate monitors (for example by Polar Electro Oy—see http://www.polarusa.com/us-en/products/get_active); and Strapless heart rate monitors (for example by Physi-Cal Enterprises Inc.—see http://mioglobal.com/-main_products).

Again, as is the case with speed measurement, these heart rate monitors merely provide the user with information about their heart rate and do not appear to permit automatic control of the intensity of human locomotion. Accordingly, these systems suffer from analogous drawbacks to those of the speed and distance measurement systems described above.

There has been some attempt in the art at control of a user's heart rate. Examples may include the BODIBEAT™ music player marketed by Yamaha—see http://www.yamaha.com/bodibeat/consumer.asp; and the TRIPLEBEAT™ application marketed by the individual Dr. Nuria Oliver—see http://www.nuriaoliver.com/TripleBeat/TripleBeat.htm.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method for the automatic control of locomotion speed in a human or other animal subject. The method comprises: estimating the subject's actual locomotion speed using one or more sensors to thereby obtain a measured speed; determining an error comprising a difference between a desired speed and the measured speed; and outputting, to the subject, a stimulus frequency signal wherein the stimulus frequency signal is based on the error in such a manner that when the subject ambulates in a manner that matches a frequency of the stimulus frequency signal, the subject's actual speed controllably tracks the desired speed.

Another aspect of the invention provides a method for the automatic control of locomotion position of a human or other animal subject. The comprises: estimating the subject's actual locomotion position using one or more sensors to thereby obtain a measured position; determining an error comprising a difference between a desired position and the measured position; and outputting, to the subject, a stimulus frequency signal wherein the stimulus frequency signal is based on the error in such a manner that when the subject ambulates in a manner that matches a frequency of the stimulus frequency signal, the subject's actual position controllably tracks the desired position.

Another aspect of the invention provides a method for the automatic control of locomotion intensity in a human or other animal subject. The method comprises: estimating the subject's actual locomotion intensity using one or more sensors to thereby obtain a measured intensity; and determining an intensity error comprising a difference between a desired intensity and the measured intensity. If an absolute value of the intensity error is outside of a threshold region around the desired intensity, then the method involves: estimating the subject's actual locomotion speed using one or more sensors to thereby obtain a measured speed; converting the desired intensity to a desired speed; determining a speed error comprising a difference between the desired speed and the measured speed; and outputting, to the subject, a speed-based stimulus frequency signal wherein the speed-based stimulus frequency signal is based on the speed error in such a manner that when the subject ambulates in a manner that matches a frequency of the speed-based stimulus frequency signal, the subject's actual intensity controllably tracks the desired intensity. If the absolute value of the intensity error is within the threshold region around the desired intensity, then the method involves outputting, to the subject, an intensity-based stimulus frequency signal wherein the intensity-based stimulus frequency signal is based on the intensity error in such a manner that when the subject ambulates in a manner that matches a frequency of the intensity-based stimulus frequency signal, the subject's actual intensity controllably tracks the desired intensity.

Another aspect of the invention provides a system for automatically controlling a locomotion speed of a human or other animal subject. The system comprises: one or more sensors for sensing one or more corresponding parameters of the locomotion movement of the subject and for generating therefrom a measured speed which represents an estimate of the subject's actual locomotion speed; a controller configured to: determine an error comprising a difference between a desired speed and the measured speed and output, to the subject, a stimulus frequency signal; wherein the stimulus frequency signal is based on the error in such a manner that when the subject ambulates in a manner that matches a frequency of the stimulus frequency signal, the subject's actual speed controllably tracks the desired speed.

Another aspect of the invention provides a system for automatically controlling a locomotion position of a human or other animal subject. The system comprises: one or more sensors for sensing one or more corresponding parameters of the locomotion movement of the subject and for generating therefrom a measured position which represents an estimate of the subject's locomotion position; a controller configured to: determine an error comprising a difference between a desired position and the measured position and output, to the subject, a stimulus frequency signal; wherein the stimulus frequency signal is based on the error in such a manner that when the subject ambulates in a manner that matches a frequency of the stimulus frequency signal, the subject's actual position controllably tracks the desired position.

Another aspect of the invention provides a system for automatically controlling a locomotion intensity of a human or other animal subject. The system comprises: one or more sensors for sensing one or more corresponding parameters of the locomotion movement of the subject and for generating therefrom a measured speed which represents an estimate of the subject's actual locomotion speed; one or more sensors for sensing one or more corresponding parameters correlated with an intensity indicator of the subject and for generating therefrom a measured intensity which represents an estimate of the subject's actual locomotion intensity; and a controller configured to: determine an intensity error comprising a difference between a desired intensity and the measured intensity; and if an absolute value of the intensity error is outside of a threshold region around the desired intensity: convert the desired intensity to a desired speed; determine a speed error comprising a difference between the desired speed and the measured speed; and output, to the subject, a speed-based stimulus frequency signal wherein the speed-based stimulus frequency signal is based on the speed error in such a manner that when the subject ambulates in a manner that matches a frequency of the speed-based stimulus frequency signal, the subject's actual intensity controllably tracks the desired intensity; and if the absolute value of the intensity error is within the threshold region around the desired intensity: output, to the subject, an intensity-based stimulus frequency signal wherein the intensity-based stimulus frequency signal is based on the intensity error in such a manner that when the subject ambulates in a manner that matches a frequency of the intensity-based stimulus frequency signal, the subject's actual intensity controllably tracks the desired intensity.

In addition to the exemplary aspects and embodiments described above, further aspects and embodiments will become apparent by reference to the drawings and by study of the following detailed descriptions.

BRIEF DESCRIPTION OF DRAWINGS

In drawings, which illustrate non-limiting embodiments of the invention.

DESCRIPTION

Figure 1A:
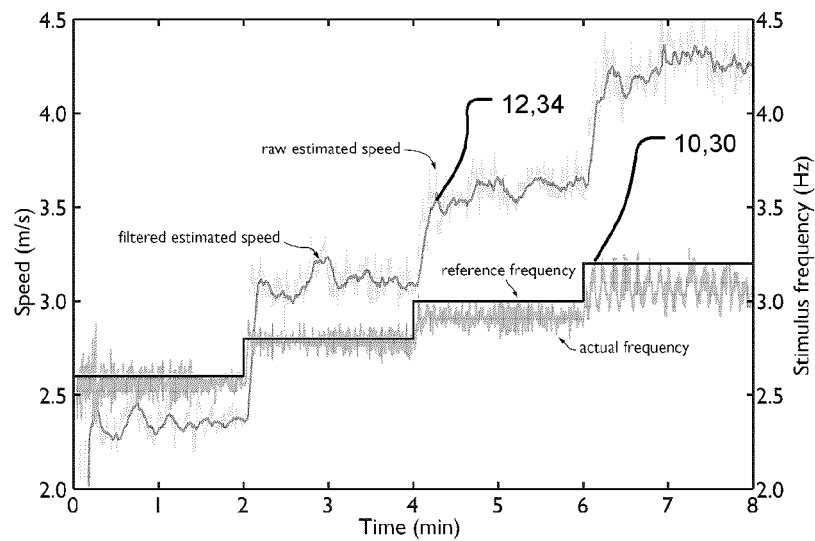
FIG. 1A is a graphical depiction of plots which show experimentally determined correlation between stimulus frequency (which is output to a subject via auditory tones and which the subject is instructed to match) and estimated running speed.

Before the embodiments of the invention are explained in detail, it is to be understood that the invention is not limited in its application to the details of construction and the arrangements of the operative components set forth in the following description or illustrated in the drawings. The invention is capable of other embodiments and of being practiced or being carried out in various ways. Also, it is understood that the phraseology and terminology used herein are for the purpose of description and should not be regarded as limiting. The use herein of "including" and "comprising", and variations thereof, is meant to encompass the items listed thereafter and equivalents thereof. Unless otherwise specifically stated, it is to be understood that steps in the methods described herein can be performed in varying sequences.

One may define the frequency of locomotion (e.g. running or walking) as the number of steps taken in a unit of time. Locomotion frequency may be measured in units of $s^{-1}$ or Hz. When a human is running and/or walking, the human exhibits a high degree of correlation (e.g. a one-to-one mapping) between their locomotion frequency and speed —i.e. when instructed or otherwise caused or motivated to run at a particular frequency, humans and other animals automatically adjust their speed accordingly. When instructed or otherwise caused or motivated to run at a higher frequency, humans will tend to run faster. When instructed or otherwise caused or motivated to run at a lower frequency, humans will tend to run slower.

Particular embodiments of the invention provide methods and systems for automatic control of the locomotion (e.g. running or walking) speed of a human or other animal subject. The methods and systems involve estimating the subject's locomotion speed using one or more sensors, determining a difference (referred to as an error) between a desired speed and the estimated speed, and outputting (to the subject) a stimulus frequency wherein the output stimulus frequency is based on the error in such a manner that when the subject runs in a manner that matches the output stimulus frequency, the subject's actual speed tracks or matches the desired speed or otherwise tends to minimize the error. Other embodiments provide automatic control of human locomotion position (rather than speed). Systems and methods of particular embodiments, help the subject's locomotion speed and/or position automatically converge to, and stay at, desired speed and position parameters (e.g. speed and/or positions profiles).

Other aspects of the invention make use of the aforementioned methods and systems for automatic locomotive speed control to assist with automatic control of the intensity of locomotion (e.g. running or walking) of a human or other animal subject. In particular embodiments, speed control is used to control the subject's locomotion speed to cause the subject's locomotion intensity to move toward a desired intensity until the subject's locomotive intensity is within a threshold range around the desired intensity. Once the subject's locomotive intensity is within the threshold range around the desired intensity, the methods and systems switch to direct automatic intensity control. The subject's locomotive intensity is estimated using one or more intensity indicators, which may be measured or otherwise determined using one or more corresponding sensors. Within the threshold range around the desired intensity, direct automatic intensity control may be effected by: determining a difference (referred to as an intensity error) between the desired intensity and the estimated intensity, and outputting (to the subject) a stimulus frequency wherein the output stimulus frequency is based on the intensity error in such a manner that when the subject runs in a manner that matches the output stimulus frequency, the subject's actual intensity tracks or matches the desired intensity or otherwise tends to minimize the intensity error. Systems and methods of particular embodiments, help the subject's locomotion intensity automatically converge to, and stay at, desired intensity parameters (e.g. intensity profiles).

A basic and well understood principle that underlies our scientific understanding of neural control of human locomotion (e.g. running and walking) is that humans use a distinct step frequency for each speed. This relationship can also be inverted—i.e. when a human is instructed or otherwise caused or motivated to match locomotion frequency to a reference frequency, a distinct speed is selected, resulting in a high degree of correlation (e.g. a one-to-one relationship) between step frequency and locomotion speed.

Figure 1B:
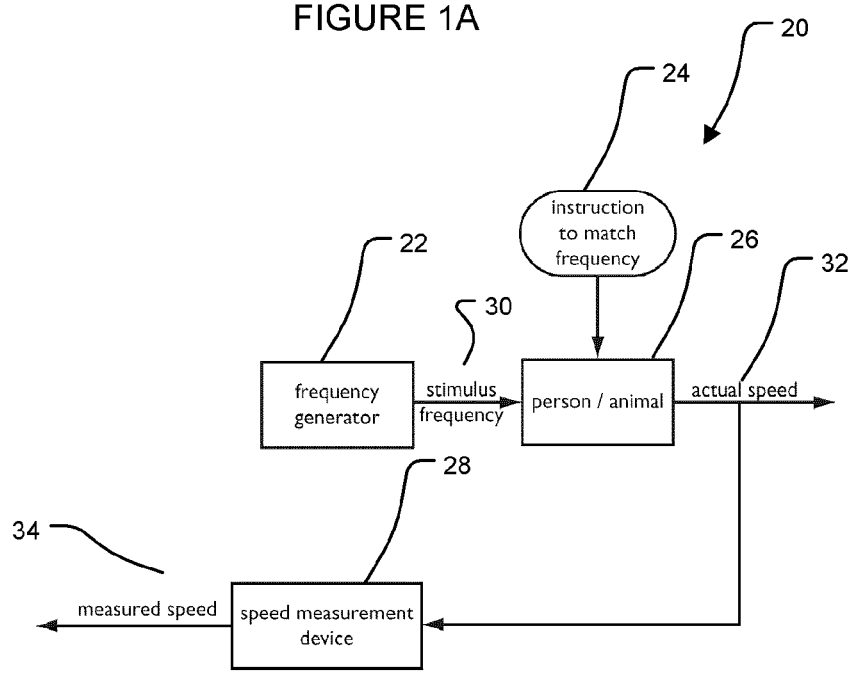
FIG. 1B is a schematic block diagram depiction of the experimental setup used to obtain the FIG. 1A plots.

FIG. 1A shows a pair of plots taken in a laboratory experiment which demonstrate the high degree of correlation in the relationship between the frequency at which a human is instructed to run (plot 10) and their resultant speed (plot 12). FIG. 1B is a schematic block diagram showing the experimental apparatus 20 giving rise to the FIG. 1A plots. As shown in FIG. 1B, a human subject 26 was instructed (instructions 24) to run in a manner which matched their step frequency to an auditory frequency stimulus 30 output (by a frequency generator 22, to subject 26) via a pair of headphones (not explicitly shown). Subject 26 ran on a 400 meter outdoor track and was free to choose their running speed (actual running speed 32). The actual running speed 32 of subject 26 was measured by a speed measurement device 28 to obtain estimated running speed 34. Estimated speed 34 sensed or otherwise detected by speed measurement device 28 may also be referred to herein as measured speed 34. In the particular case of the experiment giving rise to the plots of FIG. 1A, speed measurement device 28 involved using gyroscopic sensors 28A, 28B coupled to the subject's feet, as discussed in more detail below (see FIG. 6).

For the exemplary plots of FIG. 1A, frequency generator 22 was programmed to output a frequency stimulus signal 30 which included a series of n=4 constant reference frequencies for t=2 minute each. The frequency output stimulus 30 of frequency generator 22 is shown in FIG. 1A as frequency plot 10 and the estimated speed 34 of subject 26 is shown in FIG. 1A as speed plot 12. It can be seen from the FIG. 1A plots, that whenever a change in frequency 10 occurred, the runner automatically adjusted their speed 12, even though they were only instructed to match the frequency and not specifically instructed to adjust their speed. In addition, the adjustments to the speed 12 occurred within a few seconds after each corresponding change in frequency 10.

Figure 2:
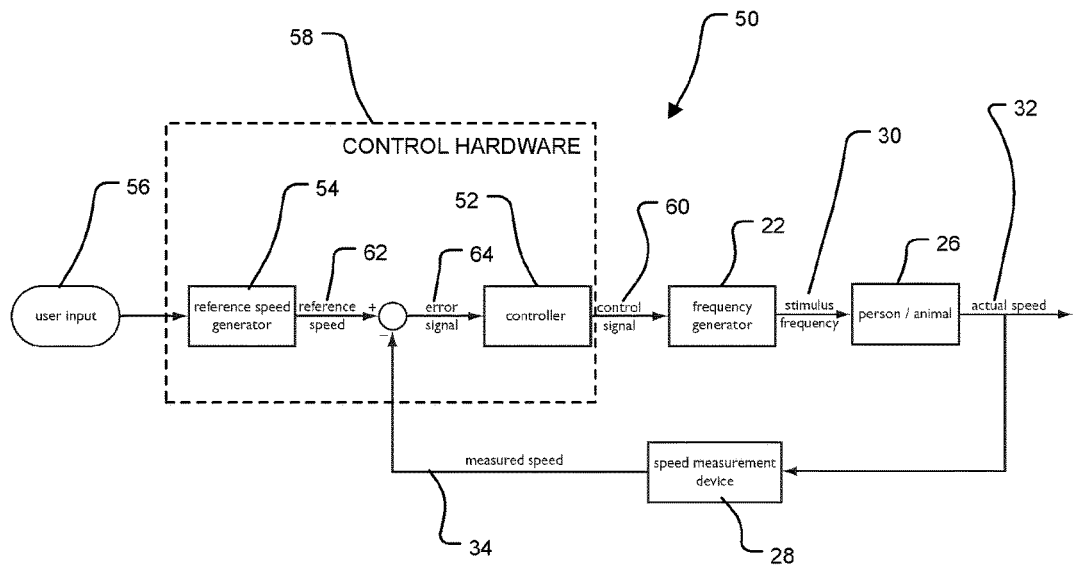
FIG. 2 is a schematic block diagram depiction of a control system for automatically controlling human/animal running/walking speed according to a particular embodiment of the invention.

FIG. 2 is a schematic block diagram of a human running/walking speed control system 50 according to a particular embodiment. Like experimental system 20 of FIG. 1B, control system 50 comprises a frequency generator 22 for outputting a stimulus frequency 30 and a speed measurement device 28 for measuring the actual running/walking speed 32 of subject 26 and outputting a measured/estimated speed 34. In particular embodiments, frequency generator 22 outputs an auditory frequency stimulus signal 30 which may be provided to subject 26 via a pair of headphones/ear buds or the like. It is envisaged, however, that in other embodiments, frequency generator 22 may provide the subject with additional or alternative forms of frequency stimulus 30 (e.g. optical and/or tactile frequency stimulus). In one currently implemented embodiment, speed measurement device 28 comprises gyroscopic sensors 28A, 28B coupled to the subject's feet, as discussed in more detail below (see FIG. 6), but it is envisaged that system 50 could make use of any suitable speed measurement device, such as any of those described herein.

Control system 50 incorporates a controller 52 which may be used to control measured speed 34 to track a desired speed (also referred to as a reference speed) 62. Controller 52 may be implemented on or by one or more suitably configured data processors, personal computers, programmable logic devices and/or the like. Controller 52 may be implemented via one or more embedded data processors or micro-electronic devices to permit system 50 to be carried with subject 26 when they are running or walking. In the illustrated embodiment, reference speed 62 is generated by a reference speed generator 54 in response to user input 56. Reference speed generator 54 may also be implemented on or by one or more suitably configured data processors, personal computers, programmable logic devices and/or the like which may be programmed with suitable user interface and speed generator software.

In the illustrated embodiment, reference speed generator 54 and controller 52 are implemented by the same hardware (e.g. one or more suitably programmed data processors) which is shown in dashed lines as control hardware 58. Control hardware 58 may perform instructions in the form of suitably programmed software. In some embodiments, control hardware 58 may be implemented in the form of one or more embedded processors that can perform substantially all of the functionality of controller 52 and reference speed generator 54. In some embodiments, control hardware 58 may interface with (e.g. plug into or wirelessly interface with) a suitably programmed computer to accept user input 56 and then the remaining functions of controller 50 and/or reference speed generator 54) may be implemented by a suitably programmed embedded processor. In still other embodiments, controller 52 and reference speed generator 54 can be implemented using separate hardware.

In some embodiments (although not specifically shown in FIG. 2), some of the functionality of speed measurement device 28 may also be implemented by control hardware 58. For example, control hardware 58 may be configured to receive information from one or more sensors (e.g. gyroscopes, GPS sensors or the like) and may process or otherwise interpret this information to determine an estimated speed 34. By way of a specific example, control hardware 58 may determine measured speed 34 by receiving two different position measurements from a position sensor (e.g. a GPS sensor) and dividing the two position measurements by an intervening time to obtain measured speed 34. In some embodiments (although not specifically shown in FIG. 2), control hardware 58 may perform some (or even all) of the functionality of frequency generator 22. For example, control hardware 58 could implement a portion of frequency generator 22 in the form a "count-down register" which outputs a pulse when it counts down from a specified period. This pulse could then be amplified and output to subject 26 via a pair of headphones or some other output device.

The operation of system 50 may be controlled by control hardware 58. Referring to FIG. 2, system 50 compares measured locomotion speed 34 with user-defined reference speed 62. System 50 generates an error signal 64 which comprises a difference between reference speed 62 and measured speed 34. Based on error signal 64, controller 52 outputs a control signal 60 which causes frequency generator 22 to change stimulus frequency 30 to minimize the speed error (i.e. error signal 64). When measured speed 34 is below reference speed 62 (i.e. error signal 64 is positive), controller 52 will output a control signal 60 which causes frequency generator 22 to increase stimulus frequency 30. Conversely, when measured speed 34 is above reference speed 62, controller 52 will output a control signal 60 which causes frequency generator 22 to decrease stimulus frequency 30. Subject 26 tends to synchronize, or can be instructed to synchronize, their movements to match stimulus frequency 30. The change in stimulus frequency 30 will lead to a corresponding change in actual locomotion speed 32 because, as discussed above, humans and other animals prefer to use a particular running/walking speed for each specified frequency. The new actual speed 32 is detected by speed measurement device 28 which outputs a new measured speed 34 which is again compared to reference speed 62 to adjust stimulus frequency 30 if desired. Stimulus frequency 30 is continually or periodically changed until measured locomotion speed 34 equals reference speed 62. System 50 thereby provides a feedback-based control system that controls actual running/walking speed 32 using a speed dependent stimulus frequency 30.

Figure 3:
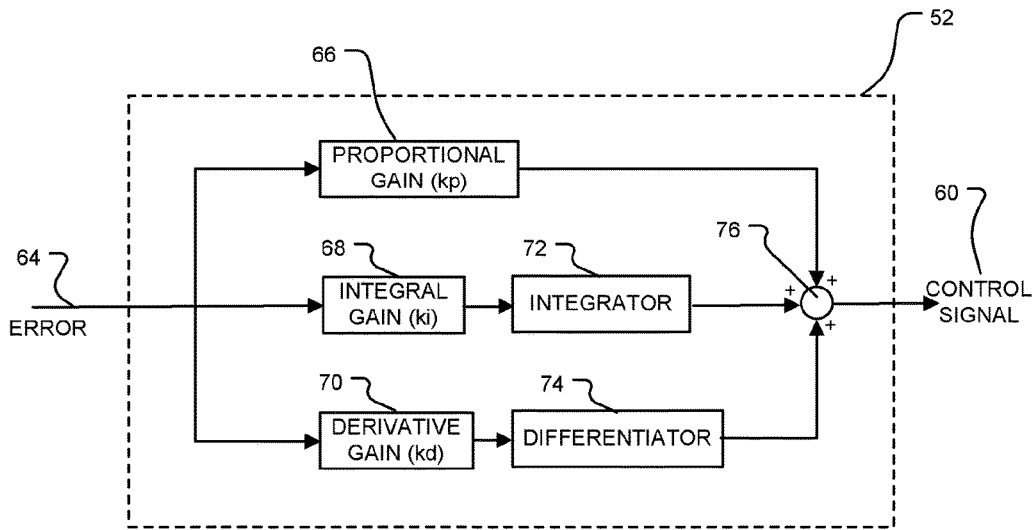
FIG. 3 is a schematic block diagram depiction of a controller of the FIG. 2 control system according to a particular embodiment of the invention.

FIG. 3 is a schematic block diagram depiction of controller 52 of the FIG. 2 control system 50 according to a particular embodiment of the invention. Controller 52 of the illustrated embodiment comprises a proportional-integral-derivative (PID) controller which receives error signal 64 and outputs a control signal 60 according to:

$$y(t) = k_p \cdot e(t) + k_d \frac{d}{dt} e(t) + k_i \int e(t) dt \quad (1)$$

where y(t) represents the control signal 60, e(t) represents the error signal 64 and $k_p$, $k_i$, $k_d$ respectively represent proportional gain 66, integral gain 68 and derivative gain 70. The integration and differentiation operators of equation (1) are respectively depicted as blocks 72, 74 of the FIG. 3 schematic depiction. Not specifically shown in the FIG. 3 depiction is a mapping between the output of summing junction 76 and a control signal 60 that is suitable for input to frequency generator 22 (see FIG. 2). In one particular implementation, frequency generator 22 outputs a stimulus frequency that matches the stimulus frequency of control signal 60. In such embodiments, a mapping may not be required between the output of summing junction 76 and control signal 60. It will be appreciated that such a mapping will depend on the particular frequency generator 22 used for any given application.

The gain parameters $k_p$, $k_i$, $k_d$ (blocks 66, 68, 70) specify the relative contribution of the proportional, integral and derivative controller parts to control signal 60. These gain parameters $k_p$, $k_i$, $k_d$ (blocks 66, 68, 70) can be adjusted (e.g. calibrated and/or experimentally determined) to optimize the controlled behavior of subject 26. The gain parameters $k_p$, $k_i$, $k_d$ (blocks 66, 68, 70) may be user-configurable constants or may be functions of other parameters (e.g. time and/or speed). In some embodiments, one or more of the gain parameters $k_p$, $k_i$, $k_d$ (blocks 66, 68, 70) may be set to zero. In some embodiments, gain parameters $k_p$, $k_i$, $k_d$ (blocks 66, 68, 70) can be configured so that the changes in stimulus frequency 30 are not overly noisy or do not exhibit overly large jumps. In other embodiments, other control techniques may be used to obtain similar results. By way of non-limiting example, in addition to or in the alternative to using the first derivative (single differentiator 74) and first integral (single integrator 72) of error signal 64 as shown in FIG. 3, some embodiments may involve higher order derivatives and/or integrators of error signal 64 to determine control signal 60.

Figure 4:
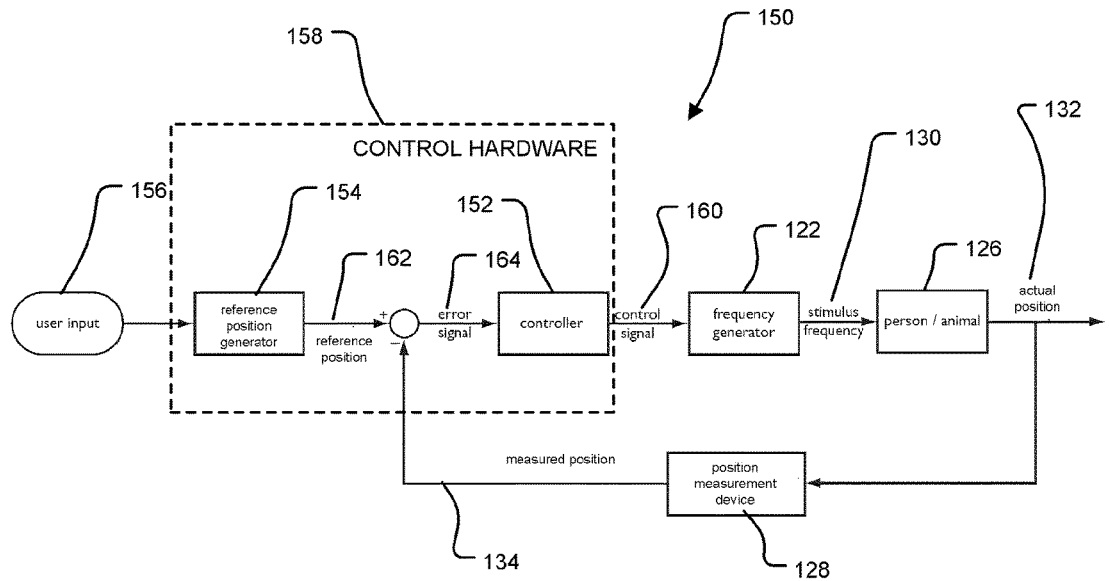
FIG. 4 is a schematic block diagram depiction of a control system for automatically controlling human running/walking position according to a particular embodiment of the invention.

FIG. 4 is a schematic block diagram of a human running/walking position control system 150 according to another particular embodiment. Position control system 150 is similar in many respects to speed control system 50 of FIG. 2, except that position control system 150 uses position (instead of speed) as the control variable. Control system 150 comprises a frequency generator 122 which outputs a stimulus frequency 130 in response to control signal 160. Frequency generator 122 may be substantially similar to frequency generator 22 of system 50. Instead of a speed measurement device, position control system 150 comprises a position measurement device 128 which outputs a measured position 134 (also referred to as an estimated position 134) of subject 126. It will be appreciated that in some embodiments, position measurement device 128 of position control system 150 may be implemented by integrating the measured speed output of a speed measurement device (e.g. measured speed output 34 of speed measurement device 28 of speed control system 50). Similarly, speed measurement device 28 of speed control system 50 could be implemented by differentiating the measured position output of a position measurement device (e.g. measured position output 134 of position measurement device 150 of position control system 150).

Position control system 150 comprises controller 152 and reference position generator 154 which may be similar to controller 52 and reference speed generator 54 of speed control system 50. In particular, controller 152 and reference position generator 154 may be implemented in any of manners discussed above for controller 52 and reference speed generator 54. In the illustrated embodiment, controller 152 and reference position generator 154 are implemented by control hardware 158.

The operation of system 150 may be controlled by control hardware 158. Referring to FIG. 4, system 150 compares measured locomotion position 134 with user-defined reference position 162. Reference position 162 may comprise a reference trajectory and/or a desired position 162 for any given time or any other suitable position information. System 150 generates an error signal 164 which comprises a difference between reference position 162 and measured position 134. Based on error signal 164, controller 152 outputs a control signal 160 which causes frequency generator 122 to change stimulus frequency 130 to attempt to minimize the position error (i.e. error signal 164). When measured position 134 is behind a desired reference position 162 (i.e. error signal 164 is positive), controller 152 will output a control signal 160 which causes frequency generator 122 to increase stimulus frequency 130 with the objective of reducing position error 164 over time. Conversely, when measured position 134 has advanced beyond a desired reference position 162, controller 152 will output a control signal 160 which causes frequency generator 122 to decrease stimulus frequency 130 with the objective of reducing position error 164 over time. Subject 26 tends to synchronize, or can be instructed to synchronize, their movements to match stimulus frequency 130. The change in stimulus frequency 130 will lead to a corresponding change in actual locomotion speed (not shown in FIG. 4) because, as discussed above, humans and other animals prefer to use a particular running/walking speed for each specified frequency. After this speed adjustment, a resultant position 132 is detected by position measurement device 128 which outputs a new measured position 134 which is again compared to reference position 162 to adjust stimulus frequency 130 if desired. Stimulus frequency 130 is continually changed until measured locomotion position 134 equals reference position 162. System 150 thereby provides a feedback system that controls actual running/walking position 132 using a position dependent stimulus frequency 130.

Controller 152 of system 150 may also be implemented by a PID control scheme similar to that shown schematically in FIG. 3, except that error signal 164 represents a position error in the case of controller 152 (rather than a speed error, as is the case in controller 52 of FIGS. 2 and 3).

Figure 8:
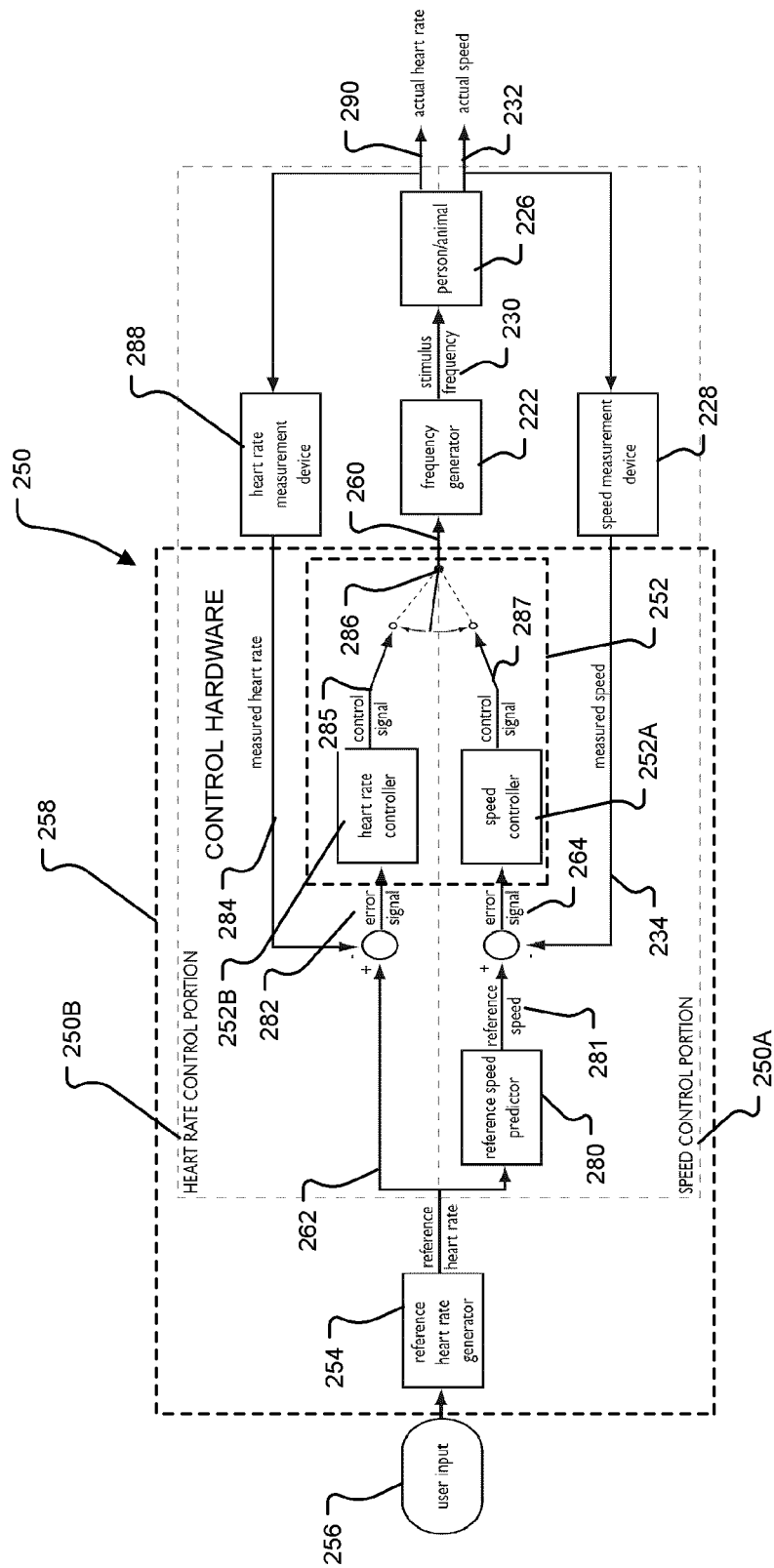
FIG. 8 is a schematic block diagram depiction of a control system for automatically controlling human running/walking intensity according to a particular embodiment of the invention.

FIG. 8 is a schematic block diagram of a human running/walking intensity control system 250 according to another particular embodiment. As mentioned above, locomotive intensity is typically estimated using one or more estimatable or measurable intensity indicators which may include, by way of non-limiting example, hear rate, metabolic rate, oxygen consumption, perceived exertion, mechanical power and/or the like. In the illustrated embodiment, control system 250 uses the heart rate of subject 226 as an intensity indicator, but this is not necessary. In other embodiments, other additional or alternative intensity indicators could be used. Intensity control system 250 is similar in some respects to speed control system 50 of FIG. 2, except that intensity control system 250 uses both speed and intensity (as reflected in the heart rate of subject 226 which is used as an intensity indicator) as control variables. As described in more detail below, intensity control system 250 uses speed control to achieve a number of advantages over intensity control alone.

Control system 250 comprises a frequency generator 222 which outputs a stimulus frequency 230 in response to control signal 260. Frequency generator 222 may be substantially similar to frequency generator 22 of system 50. Control system comprises a speed measurement device 228 which may be substantially similar to speed measurement device 28 of system 50 and which senses actual speed 232 of subject 226 and outputs a measured speed 234 (also referred to as an estimated speed 234) of subject 226. In addition to speed measurement device, system 250 comprises a heart rate measurement device 288 which senses actual heart rate 290 of subject 226 and outputs a measured heart rate 284 (also referred to as an estimated heart rate) of subject 226.

Intensity control system 250 also comprises a reference heart rate generator 254 which may be similar to reference speed generator 54 of speed control system 50. In particular, reference heart rate generator 254 may be implemented in any of manners discussed above for reference speed generator 54. In the illustrated embodiment, reference heart rate generator 254 is implemented by control hardware 258. Reference heart rate generator 254 outputs a reference heart rate 262 and intensity control system 250 attempts to cause the actual heart rate 290 of subject 226 to track the reference heart rate 262. Reference heart rate generator 254 may output reference heart rate 262 in response to user input 256.

Intensity control system 250 comprises a controller 252 which may be similar to controller 52 of speed control system 50. In the illustrated embodiment, controller 252 is implemented by the same control hardware 258 as reference heart rate generator 254. For the purposes of the schematic illustration of FIG. 8, controller 252 is shown to comprise a speed controller 252A, a heart rate controller 252B and a control region switch 286. As will be discussed in more detail below, speed controller 252A effects speed control in a manner similar to that discussed above for speed control system 50, heart rate controller 252B effects heart rate control and control region switch 286 switches system 250 between heart rate control and speed control. It will be appreciated, especially in view of the description to follow, that in practice, speed controller 252A, heart rate controller 252B and control region switch 286 may be implemented by the same logic (e.g. a suitably programmed processor or the like).

Intensity control system 250 also comprises a reference speed predictor 280 which receives, as input, reference heart rate signal 262 and outputs a corresponding reference speed 281. Reference speed predictor 280 may be implemented on or by one or more suitably configured data processors, personal computers, programmable logic devices and/or the like which may be programmed with suitable user interface and speed generator software. In the illustrated embodiment, reference speed predictor 280 is implemented by the same control hardware 258 as reference heart rate generator 254 and controller 252.

In converting an input reference heart rate signal 262 into an output reference speed signal 281, reference speed predictor 280 may be configured to implement a model which maps human (or animal) heart rate to locomotive speed. Such models are well known in the art and include, by way of non-limiting example, the model proposed by Hermansen L & Saltin B (1969). Oxygen uptake during maximal treadmill and bicycle exercise. Journal of Applied Physiology, 26: 31-37 which is hereby incorporated herein by reference. Reference speed predictor 280 may incorporate or consider subject specific data (e.g. calibration data). Such subject specific data may be incorporated into the heart rate to locomotive speed mapping model implemented by reference speed predictor 280 or may otherwise be incorporated into the heart rate to locomotive speed conversion algorithms of reference speed generator 280. Such subject specific calibration data may comprise one or more simultaneous measurements of heart rate and locomotive speed for subject 226—for example, subject 226 may run on a track and their locomotive speed and heart rate may be simultaneously measured at one or more times.

In one particular embodiment, subject specific calibration data may be used in the following manner. Once one or more simultaneous measurements of heart rate and locomotive speed are obtained for subject 226, as described above, the heart rate to locomotive speed mapping model is used to calculate a model-predicted locomotive speed at the heart rates measured during calibration. These model-predicted speeds may be compared to the measured speeds to generate corresponding model errors. Some sort of average may be taken of these model errors and this average model error may be used by reference speed generator 280 to predict an output reference speed signal 281 from reference heart rate signal 262. More particularly, the result of the heart rate to locomotive speed mapping model may be offset by the average model error to obtain output reference speed 281.

In another particular embodiment, the heart rate to locomotive speed mapping model may itself be calibrated with subject specific calibration data. For example, subject 226 may go on a specific calibration run, which may guide subject 226 through a series of speeds while measuring the corresponding heart rate at each speed. Still another alternative involves using historical data from previous workouts (e.g. from previous uses of system 250) to find instances when the heart rate of subject 226 is in a steady state and to record the corresponding locomotive speeds. Such use of historical data may be able to work without pre-calibration and may be constantly updated based on the present fitness status of subject 226. If enough user specific calibration data is collected, then reference speed generator 280 may use this user specific calibration data without having to rely on a heart rate to locomotive speed mapping model.

In practice, either or both of the heart rate to locomotive speed mapping model and the user specific calibration data used by reference speed generator 280 may be stored in a look up table or the like in accessible memory (not shown) which may be part of control hardware 258.

In operation, intensity control system 250 controls the locomotive intensity of subject 226 (as indicated, in the illustrated embodiment, by the heart rate of subject 226 which represents one or many possible intensity indicators which could be used by system 250). Although locomotion speed and intensity are highly correlated, external disturbances like wind and/or terrain changes, and internal disturbances such as fatigue, influence the relationship between locomotion speed and intensity. Locomotion intensity control system 250 leverage speed control (as implemented by speed control portion 250A) to assist heart rate control portion 250B to accurately control locomotive intensity (heart rate).

In theory, heart rate control portion 250B could be implemented without the use of additional speed control portion 250A to effect heart rate control—e.g. heart rate controller 252B could output a heart rate control signal 285 which would become an input signal 260 to frequency generator 222 and which would cause frequency generator 222 to output a stimulus frequency 230 which, when followed by subject 226, minimizes the heart rate error 282 between reference heart rate 262 and the measured heart rate 284 of subject 226. If, for example, measured heart rate 284 is below reference heart rate 262, heart rate controller 252B would output a heart rate control signal 285 which would cause frequency generator 222 to increase stimulus frequency 230 to cause a corresponding increase in the speed of subject 226 which in turn would increase the actual and measured heart rate 290, 284 of subject 226.

However, heart rate dynamics are slow. Physiological research has determined that after a change in locomotion speed, it may take several minutes for the heart rate to reach a steady state corresponding to the new locomotive speed. As a result of these slow heart rate dynamics, controlling heart rate based purely on the difference between a reference heart rate (e.g. reference heart rate 262) and a measured heart rate (e.g. measured heart rate 284) can be problematic. For example, if a user's measured heart rate is below the reference heart rate, the controller will increase the stimulus frequency to minimize the heart rate error. In response to this increased stimulus frequency, the user will increase his or her locomotive speed. However, because it takes time for the user's heart rate to reach a steady state value corresponding to this new speed, the controller will continue to increase the stimulus frequency. Typically, this will result in overshoot and/or oscillation of the reference heart rate (and corresponding overshoot and/or oscillation of speed) because the user's speed is increased beyond the speed that would result in the reference heart rate. These issues are the most apparent when there is a large initial error between the reference and measured heart rates.

These issues may be overcome to some degree by suitable selection of control parameters, but the resulting control is undesirably slow. These issues may also be overcome to some degree by controlling heart rate relatively loosely—e.g by accepting actual heart rates that are within a large margin of error with respect to the reference heart rate. These potential solutions do not allow for accurate and rapid control of the heart rate.

Intensity control system 250 of the illustrated embodiment overcomes this issue by leveraging speed control (implemented by speed control portion 250A) to bring measured heart rate 284 close to reference heart rate 262 (e.g. within a threshold region around reference heart rate 262) and limiting the use of heart rate control (implemented by heart rate control portion 250B) to provide fine adjustment once measured heart rate 284 of subject 226 is close to reference heart rate 262 (e.g. within the threshold region around reference heart rate 262). The threshold region around reference heart rate 262 may be a user-configurable parameter of system 250 or may be a predefined parameter of system 250. The threshold region around reference heart rate 262 may be defined in a number of different ways. By way of non-limiting example, the threshold region may be specified to be the reference heart rate±x beats per minute or the reference heart rate±x % of the reference heart rate, where x may be a user-configurable threshold region parameter.

If measured heart rate 284 is outside of the threshold region around reference heart rate 262, then control system 250 will use speed control portion 250A which may be considered (in the schematic depiction of FIG. 8) to mean that control region switch 286 is configured to connect speed control signal 287 from speed controller 252A to input 260 of frequency generator 222. It will be appreciated by those skilled in the art, that control region switch 286 may not be physically present as a switch and may be implemented (e.g. in software) by controller 252. Speed control portion 250A of system 250 attempts to output a stimulus frequency 230 which will cause subject 226 to increase or decrease their locomotive speed so as to move their actual and measured heart rates 290, 284 toward reference heart rate 262. Speed control portion 250A uses reference speed predictor 280 discussed above to convert reference heart rate 262 into a reference speed 281. Once this reference speed 281 is obtained, the operation of speed control portion 250A of system 250 is substantially similar to the operation of speed control system 50 described above, while measured heart rate 284 is outside the threshold region around reference heart rate 262.

Controller 252 may monitor the heart rate error signal 282 (which reflects the difference between measured heart rate 284 and reference heart rate 262). Once heart rate error signal 282 is sufficiently small (i.e. measured heart rate 284 is within the threshold region around reference heart rate 262), system 250 switches to heart rate control. This may be considered (in the schematic depiction of FIG. 8) to mean that control region switch 286 is switches to connect heart rate control signal 285 from heart rate controller 252B to input 260 of frequency generator 222. Thereafter, intensity control system effects control of heart rate. In some embodiments, if the heart rate error 282 goes outside of the threshold region around reference heart rate 262, then control system 250 may switch back to speed control, but this is not necessary. In some embodiments, control system 250 may also switch from speed control to heart rate control in other circumstances. By way of non-limiting example, control system 250 may switch from speed control to heart rate control if speed control does not bring measured heart rate 284 to within the threshold region around reference heart rate 262 within a threshold period of time. Such a threshold period of time may be a user-configurable parameter.

The operation of control system 250 in heart rate control mode (e.g. the operation of heart rate control portion 250B) may be similar to the various control systems described above. Referring to FIG. 8, heart rate control portion 250B compares measured heart rate 284 with user-defined reference heart rate 262. Reference heart rate 262 may comprise a reference trajectory and/or a desired heart rate 262 for any given time or any other suitable heart rate information. Heart rate control portion 250B generates a heart rate error signal 282 which comprises a difference between reference heart rate 262 and measured heart rate 284. Based on heart rate error signal 282, heart rate controller 252B outputs a heart rate control signal 285 which is received by frequency generator 222 as input signal 260 and which causes frequency generator 222 to change stimulus frequency 230 with the objective of minimizing heart rate error 282. When measured heart rate 284 is below a desired reference heart rate 262 (i.e. heart rate error signal 282 is positive), heart rate controller 252B will output a heart rate control signal 285 which causes frequency generator 222 to increase stimulus frequency 230 with the objective of reducing heart rate error 282 over time. Conversely, when measured heart rate 284 is greater than a desired reference heart rate 262, heart rate controller 252B will output a heart rate control signal 285 which causes frequency generator 222 to decrease stimulus frequency 230 with the objective of reducing heart rate error 282 over time. Subject 226 tends to synchronize, or can be instructed to synchronize, their movements to match stimulus frequency 230. The change in stimulus frequency 230 will lead to a corresponding change in actual locomotion speed 232 because, as discussed above, humans and other animals prefer to use a particular running/walking speed for each specified frequency. After this speed adjustment, a resultant heart rate is detected by heart rate measurement device 288 which outputs a new measured heart rate 284 which is again compared to reference heart rate 262 to adjust stimulus frequency 230 if desired. Stimulus frequency 230 is continually changed until measured heart rate 284 equals reference heart rate 262. System 250 thereby provides a feedback system that controls actual heart rate 290 using a heart rate dependent stimulus frequency 230.

The profile of a reference speed 62 (and the corresponding user input 56 to reference speed generator 154), the profile of a reference position 162 (and the corresponding user input 156 to reference position generator 154) and/or the profile of a reference heart rate 262 (and the corresponding user input 256 to reference heart rate generator 254) may take a variety of forms. By way of non-limiting example, in the case of speed control, a user may specify:

- the total time to cover a certain distance (e.g. 50 min for a 10 km race). The user may also specify that the distance is to be run at a constant speed or that the speed should have some profile (e.g. starting a relatively high speed, stepping down slightly to a middle speed and then increasing for a "kick" at the end of the race).
- an interval training regime, which will guide the subject through a series of predetermined or user-configurable speeds (e.g. 5 min at 3 m/s, 2 min at 3.5 m/s, 1 min at 4 m/s etc. or 2 km at 3 m/s, 1 km at 3.5 m/s, 1 km at 4 m/s, etc.).
- a training or race profile that increases speed when only a certain amount of time or distance remains.
- a completely user-configurable profile for training or racing purpose; and/or
- the like.

In addition to or in the alternative to a user inputting a training or race profile, such a profile could be input by a real or virtual trainer. The training or race profile can also be changed on the fly by the user or trainer changing reference speed 62 or position 162 or heart rate 262. It is also possible for a user to download data (e.g. another person's speed profile data from the other person's workout at a distant place and/or time). A training or race profile based on this data can then be input so that the user can virtually train with, or race against, this other person.

Figure 5:
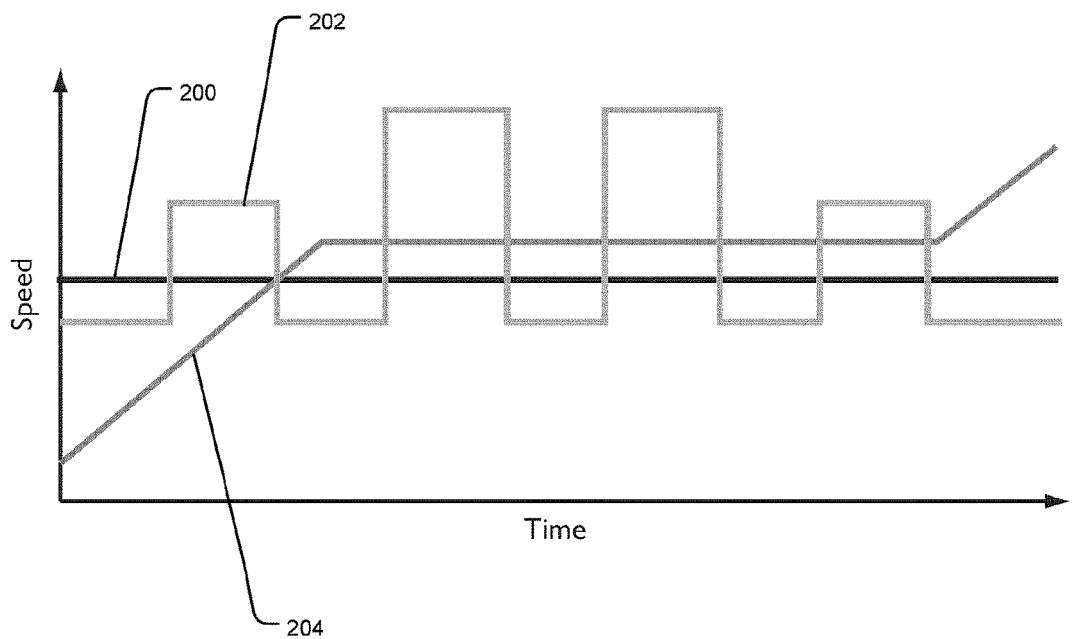
FIG. 5 is a schematic depiction of a number of reference speed profiles that could be generated by the FIG. 2 reference speed generator in response to user input.

FIG. 5 schematically depicts a number of exemplary and non-limiting speed profiles (i.e. profiles for desired/reference speed 162) including constant speed profile 200, interval speed profile 202 and ramping speed profile 204. It will be appreciated that position and/or heart rate profiles similar to any of the above-discussed speed profiles could be generated by reference position generator 154 in response to user input 156 and/or by heart rate generator 254 in response to user input 256.

Speed measurement device 28 can be implemented using a variety of different techniques and speed measurement apparatus. A number of technologies capable of measuring running/walking speed are discussed above. Various different sensors may be used, individually or combined with other sensors, to implement such speed measurement apparatus. By way of non-limiting example, signals from accelerometers, GPS, gyroscopes, optical and electromagnetic sensors can be processed to provide locomotion speed and information. Various processing techniques may be used to extract speed and/or position information from such sensors. The particular nature of the processing depends on the type of sensors used. Signals from such sensors may be combined with one another in an attempt to improve the accuracy of estimated speed 34. Such sensor combination can involve state estimation techniques such as Kalman-filtering, for example. Similarly, position measurement device 128 can be implemented using a variety of different techniques and position measurement apparatus. For some speed or position measurement devices 28, 128, a calibration procedure might be desirable, whereas other speed or position measurement devices 28, 128 could provide accurate speed or position estimates 34, 134 without user calibration. Heart rate measurement device 288 can similarly be implemented using a variety of techniques known in the art, such as strapped and/or strapless heart rate measurement systems.

Stimulus frequency 30, 130, 230 can be output to subject 26, 126, 226 in a variety of ways and may target different sensory systems of subject 26, 126, 226. One particular embodiment, makes use of an auditory metronome which outputs an auditory frequency stimulus signal 30, 130, 230 to subject 26, 126, 226. Another implementation using auditory signals involves the use of music as frequency stimulus 30, 130, 230. For example, the frequency (tempo) of music could be controlled so that either songs with the right frequency are selected, or the frequency of a song is adjusted to better match the intended locomotion frequency. Frequency stimulus 30, 130, 230 could also be implemented as a tactile stimulus, either by mechanical or electrical stimulation to different body parts (heel, back, arm, wrist etc.). Also, frequency stimulus 30, 130, 230 could be provided visually, for example by projecting it on the inside of a pair of glasses or in some other location visible to subject 26, 126, 226.

Control signals 60, 160, 285, 287 (and corresponding stimulus frequency 30, 130, 230) can be updated whenever estimated speed/position/heart rate 34, 134, 234, 284 is updated and may be accomplished, in one particular example, by continually changing the frequency of a metronome or the tempo of a song. Such relatively short control periods may occur, for example, in time periods on the order of tens of milliseconds. In some situations, it might be more comfortable for the subject if control signal 60, 160, 285, 287 (and corresponding stimulus frequency 30, 130, 230) were only updated at longer control intervals. Such longer control periods may be on the order seconds, tens of seconds or even minutes. Such control periods may not be temporally constant—for example when music is used as stimulus frequency 30, 130, 230 a control period may correspond to the length of a particular song and an update to control signal 60 (and stimulus frequency 30) can be provided each time that a new song is selected.

In such embodiments, controller 52, 152, 252 may establish a relationship between stimulation frequency 30, 130, 230 and subject-specific locomotion speed and/or heart rate. Such a relationship may be used to predict the locomotion speed or heart rate that subject 26, 126, 226 is likely to adopt when a certain song is played. This relationship between stimulation frequency and locomotion speed or heart rate can be calibrated on a subject specific basis. For example, the relationship between stimulation frequency and locomotion speed or heart rate may be calibrated using a speed interval regime, where subject 26, 126, 226 is guided through a number of different speeds. Control signals 60, 160, 285, 287 could also only be played when the measured speed, position or heart rate is outside a threshold range (e.g. a user configurable threshold range), in order to return subject 26, 126, 226 to the reference speed, position or heart rate. Current estimated step frequency may be used as the initial value for stimulus frequency 30, 130, 230. This frequency will then be adjusted by the control system to return subject 26, 126, 226 to the target speed, position or heart rate.

Figure 6:
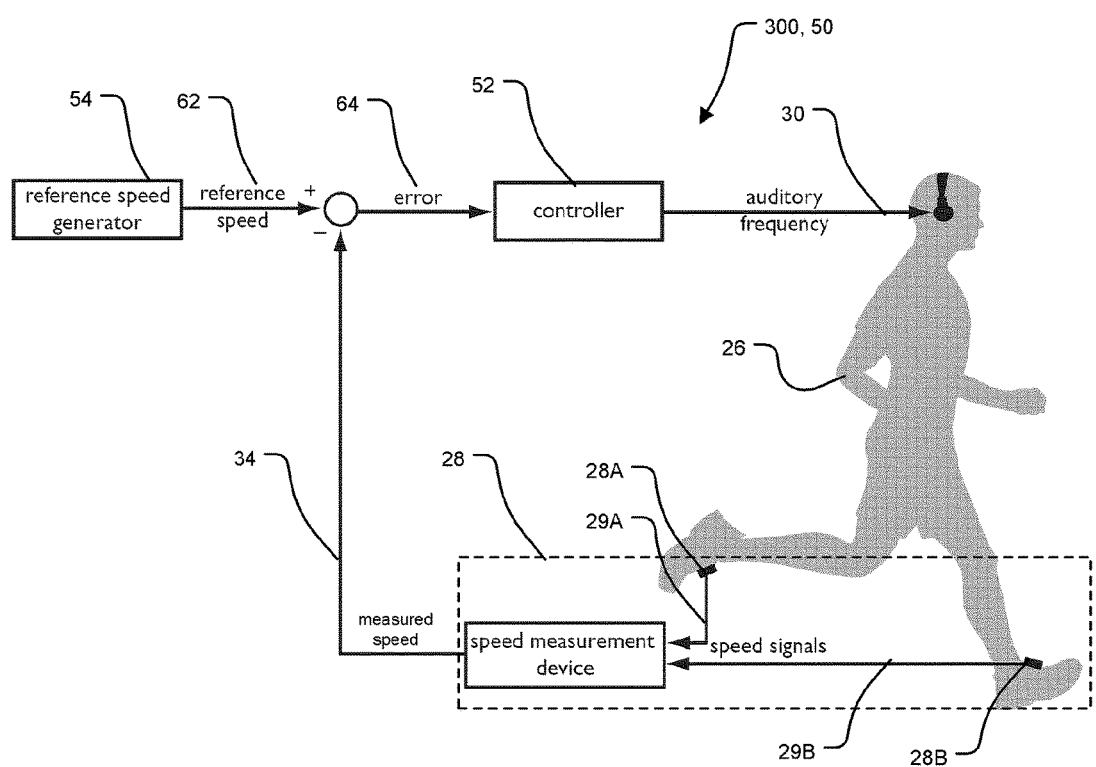
FIG. 6 depicts one particular implementation of the FIG. 2 control system according to a particular embodiment.

FIG. 6 depicts one particular implementation 300 of a control system 50 according to a particular embodiment. In the FIG. 6 implementation 300, a suitably programmed tablet personal computer (not shown), which may be carried by subject 26 in a backpack, is used to implement reference speed generator 54, a speed detection algorithm (not shown) used by speed measurement device 28 and controller 52. In the FIG. 6 implementation 300, controller 52 also performs the function of frequency generator 22 (see FIG. 2). Speed measurement device 28 comprises a pair of gyroscopes 28A, 28B attached to the feet of subject 26. Frequency stimulus 30 is provided to subject 26 via a pair of headphones for auditory stimulation (e.g. as a metronome).

The FIG. 6 implementation uses foot-mounted gyroscopes 28A, 28B to sense the running speed of subject 26. Gyroscopes 28A, 28B generate corresponding gyroscope sensor signals 29A, 29B. As is known in the art, gyroscope sensor signals 29A, 29B exhibit characteristic events that permit robust detection of foot touchdown and lift-off. By processing gyroscope signals 29A, 29B and identifying these events, speed measurement device 28 determines an estimate of the amount of time each foot spends on the ground during each step (contact time). This contact time information, in combination with a predetermined relationship between contact time and running speed, provides estimated speed 34. In some embodiments, estimated speed 34 may be determined as the moving average of the speed estimates over the previous number (e.g. two) steps. Those skilled in the art will recognize that this implementation of speed measurement device 28 represents one particular embodiment and that there are a variety of additional or alternative techniques for generating estimated running/walking speed 34.

Controller 52 of the FIG. 6 implementation 300 makes use of a discrete PID control scheme of the type shown schematically in FIG. 3 to control the running speed of subject 26. Estimated running speed 34 is compared to reference speed 62 to find error signal 64. Error signal 64 is sent to the different branches of controller 52 to implement the control scheme of FIG. 3 and equation (1). In the current embodiment, the gain parameters $k_p$, $k_i$, $k_d$ (blocks 66, 68, 70) are constant. Controller 52 of the FIG. 6 implementation 300 incorporates a frequency generator. Consequently, controller 52 outputs an updated stimulus frequency 30 in the form an auditory stimulus which is delivered to subject 26 via the illustrated earphones. In the current embodiment, stimulus frequency 30 is updated at each control step.

Figure 7:
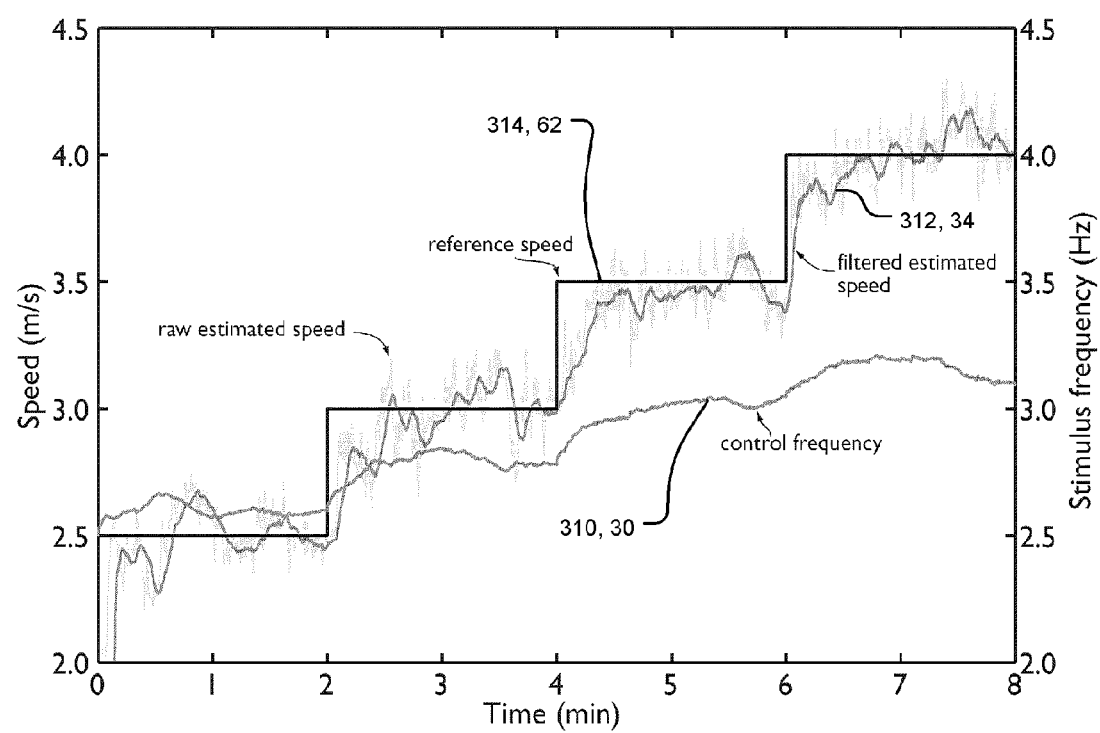
FIG. 7 is a graphical depiction of plots which show the operation of the FIG. 6 implementation.

FIG. 7 is a graphical depiction of plots which show the operation of the FIG. 6 implementation. More particularly, FIG. 7 includes plot 314 of desired/reference speed 62 output by reference speed generator 54, plot 310 of auditory stimulus frequency 30 output by controller 52 and plot 312 of the estimated speed 34 of subject 26 as estimated by speed measurement device 28. The FIG. 7 data was once again obtained by having subject 26 run on a 400 meter outdoor track. Subject 26 was instructed to try to match their step frequency to the auditory stimulus frequency 30, but was free to choose their running speed. Reference speed generator 54 was programmed to guide subject through a speed interval regime incorporating a series of n=4 constant reference speeds 62 for t=2 minute each. Plots 312 and 314 show that estimated speed 34 of subject 26 converges rapidly toward each reference speed 62 and, on average, stayed at that reference speed 62 until the reference speed 62 changed again.

Figure 9:
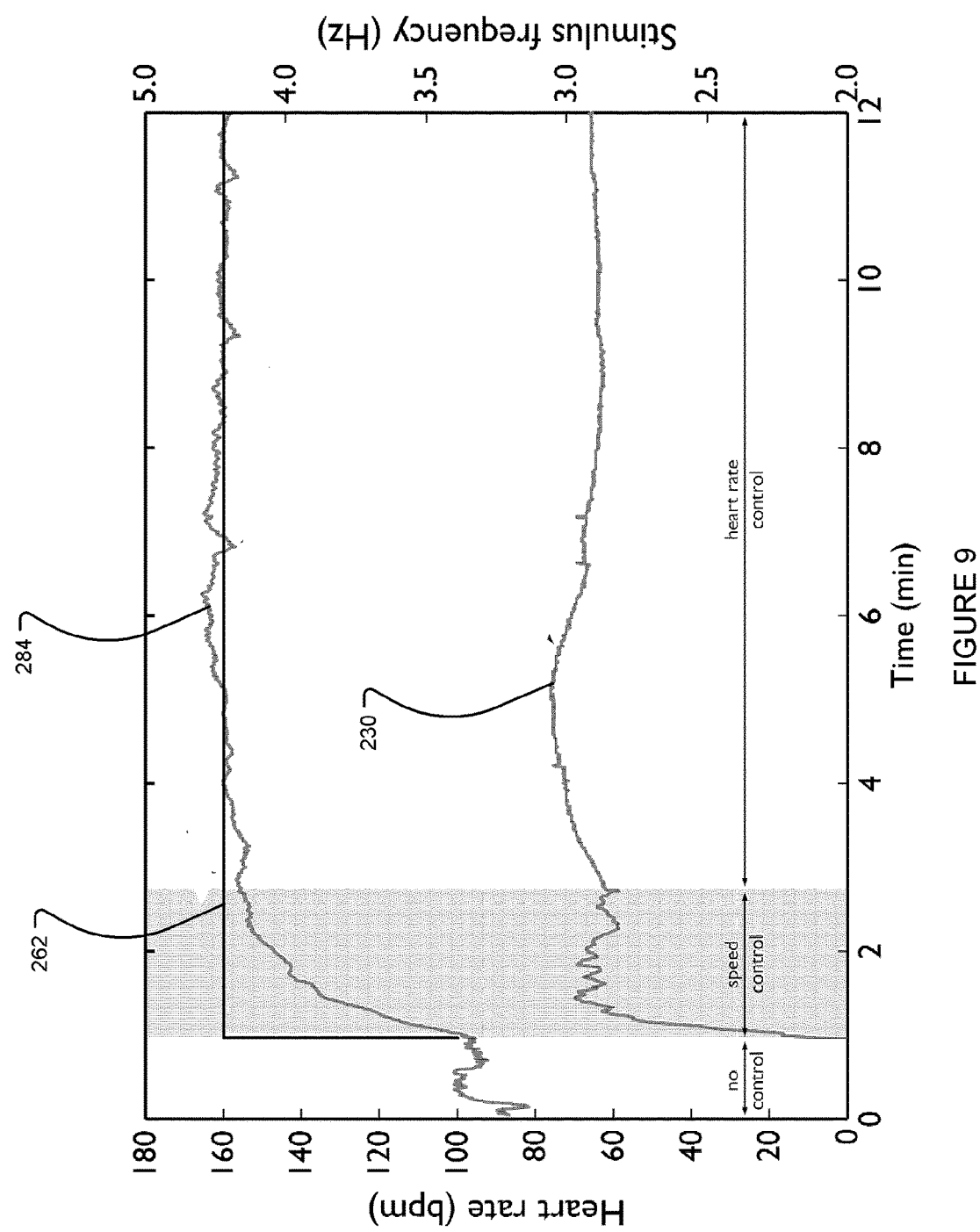
FIG. 9 is a graphical depiction of plots which show the operation of the FIG. 8 system for the control of locomotion intensity.

FIG. 9 is a graphical depiction of plots which show the operation of the FIG. 8 intensity control system 250. More particularly, FIG. 9 includes plots of desired/reference heart rate 262, a plot of the auditory stimulus frequency 230 and a plot of measured heart rate 284 of subject 226 as given by heart rate measurement device 288. The FIG. 9 data was once again obtained by having subject 226 run on a 400 meter outdoor track. Subject 226 was instructed to try to match their step frequency to auditory stimulus frequency 230, but was free to choose their running speed. Reference heart rate generator 254 was programmed to keep subject 226 at a constant heart rate of 160 beats per minute (bpm). FIG. 9 shows that measured heart rate 284 converged to reference heart rate 262 and then stayed at reference heart rate 262. Under speed control (the grey-colored region of FIG. 9), measured heart rate 284 climbs quickly up to a region of reference heart rate 262 without overshoot (although in some instances there may be some overshoot). Once measured heart rate 284 reaches a region close to reference hear rate 262, the control switches to intensity control and measured heart rate 284 tracks reasonably close to reference heart rate 262.

Variations and modifications of the foregoing are within the scope of the present invention. It is understood that the invention disclosed and defined herein extends to all the alternative combinations of two or more of the individual features mentioned or evident from the text and/or drawings. All of these different combinations constitute various alternative aspects of the present invention. The embodiments described herein explain the best modes known for practicing the invention. Aspects of the invention are to be construed to include alternative embodiments to the extent permitted by the prior art. For example:

- It will be appreciated that the above-described PID control schemes represent one particular control scheme for implementing speed and/or position control of human walking/running according to one particular embodiment. Other embodiments may incorporate other control schemes. Such other control schemes may also be based on the error between desired speed and/or position and estimated speed and/or position. Such other control schemes may also be based on controlling a stimulus frequency output to the subject.
- The control systems described above are representative examples only. Control systems in other embodiments could be modified to be more adaptive. For example, control systems could be designed to adaptively and dynamically adjust reference speed 62 (or reference position 162 or reference heart rate 262) in response to feedback information. By way of non-limiting example, such feedback information could comprise current and historical values for estimated speed 34, 234 and/or estimated position 134 and/or estimated heart rate 284 and/or derivatives, integrals or other functions of these values. In one example, user input 56, 156 could specify that subject 26, 126 would like to cover 10 km in 50 minutes. A dynamic speed/position controller could then help to guide subject 26, 126 toward the appropriate speed/position to establish this objective by updating reference speed/position 62, 162 and minimizing error 64, 164 to achieve this objective. If, for some reason, subject 26, 126 is unable to keep up with to desired speed/position 62, 162, the controller might detect this and decide to slow down desired speed/position 62, 162 temporarily. When subject 26, 126 is able to keep up again, the controller could decide to increase the desired speed/position 62, 162 again, in order to get closer to the original objective. Additionally or alternatively, control systems could adaptively modify gain parameters of controller 52, 152, 252 (e.g. $k_p$, $k_i$, $k_d$ (blocks 66, 68, 70) to improve performance of the control system, such as, by way of non-limiting example, by adjusting rise times, adjusting settling times and/or overshoot.
- As is known in the art, humans have the tendency to synchronize their movements to external stimuli, even when not explicitly instructed to do so. Consequently, it may not be necessary to instruct or train subject 26, 126, 226 to match external frequency stimulus 30, 130, 230—this entrainment may happen naturally.

Applications of this invention are not limited strictly to walking and running. Various embodiments may be directed toward other locomotion activities (e.g. snowshoeing, cross-country skiing, speed skating, inline skating and/or the like) and/or other activities involving cyclic movements (e.g. swimming, cycling, wheel chair racing and/or the like).

The above description relates to human subjects. However, the invention is not limited to application to humans. Particular embodiments of the invention may have application to other animals, including, for example, horses, dogs and/or other animals used for racing.

Control systems of particular embodiments may be used for rehabilitation of patients with various diseases or injuries affecting locomotion ability, including but not limited to stroke patients, Parkinson's patients, patients having spinal cord injuries, amputees, etc.

In the description above, intensity control system 250 is described in terms of a particular intensity indicator—i.e. heart rate. Heart rate is one of a variety of possible intensity indicators which may be used alone or in combination to effect intensity control in a manner analogous to that of control system 250. References to heart rate in the description above should be understood to incorporate the possibility of using other intensity indicator(s). Similarly references to components or features of control system that reference heart rate (e.g. heart rate measurement device 288, measured heart rate signal 284, heart rate controller 252B, etc.) should be understood to include the possibility of other intensity indicator(s)

What is claimed is:

1. A method for guiding locomotion speed in a human during a locomotion event, the method comprising:
    estimating the subject's actual locomotion speed during the locomotion event using one or more sensors to thereby obtain a measured speed as a distance per unit time;
    determining an error as a distance per unit time during the locomotion event, the error comprising a difference between a desired speed at a particular instant during the locomotion event as a distance per unit time and the measured speed for the particular instant during the locomotion event; and
    outputting, to the subject during the locomotion event, a stimulus frequency signal comprising a tempo wherein the tempo of the stimulus frequency signal is based on the error in such a manner that when the subject ambulates with a gait frequency that matches the tempo of the stimulus frequency signal, the subject's actual speed as a distance per unit time during the locomotion event controllably tracks the desired speed;
    wherein outputting the stimulus frequency signal based on the error comprises determining a first control term proportional to the error which is used, at least in part, to determine the stimulus frequency signal; and
    wherein outputting the stimulus frequency signal based on the error comprises determining a second control term proportional to a time integral of the error which is used, at least in part, to determine the stimulus frequency signal.

2. A method according to claim 1 wherein outputting the stimulus frequency signal based on the error comprises implementing a proportional-integral-derivative (PID) control scheme.

3. A method according to claim 2 wherein implementing the PID control scheme comprises generating a control signal based on the error and using the control signal as an input to a frequency generator which outputs the stimulus frequency signal in response to the control signal.

4. A method according to claim 1 wherein outputting the stimulus frequency signal based on the error comprises generating a control signal as a combination of available control terms and using the control signal as an input to a frequency generator which outputs the stimulus frequency signal in response to the control signal.

5. A method according to claim 4 comprising updating the control signal with a control period of less than 10 seconds.

6. A method according to claim 4 comprising updating the control signal with a control period of less than 1 second.

7. A method according to claim 4 wherein the stimulus frequency signal is provided to the subject in a form of music and the control signal is updated at a conclusion of each musical piece.

8. A method according to claim 1 wherein the stimulus frequency signal comprises an auditory signal that is output to the subject.

9. A method according to claim 1 wherein the stimulus frequency signal comprises one or more of: a tactile signal that is output to the subject and a visual signal that is output to the subject.

10. A method according to claim 1 wherein the desired speed comprises a user-specified speed profile.

11. A method according to claim 10 wherein the user-specified speed profile comprises an interval profile which comprises a plurality of intervals with each interval comprising at least one of: a desired speed level for a desired period of time; and a desired speed level for a desired distance.

12. A method according to claim 10 wherein the user-specified speed profile comprises a ramping speed profile which includes one or more time periods when the desired speed is increasing constantly with time.

13. A method according to claim 10 wherein the user-specified speed profile comprises a profile downloaded from a communication network.

14. A method according to claim 4 wherein the stimulus frequency signal is provided to the subject in a form of music and the control signal is updated at one or more intervals within a musical piece.

15. A method for guiding locomotion speed in a human during a locomotion event, the method comprising:
    estimating the subject's actual locomotion speed during the locomotion event using one or more sensors to thereby obtain a measured speed as a distance per unit time;
    determining an error as a distance per unit time during the locomotion event, the error comprising a difference between a desired speed at a particular instant during the locomotion event as a distance per unit time and the measured speed for the particular instant during the locomotion event; and
    outputting, to the subject during the locomotion event, a stimulus frequency signal comprising a tempo wherein the tempo of the stimulus frequency signal is based on the error in such a manner that when the subject ambulates with a gait frequency that matches the tempo of the stimulus frequency signal, the subject's actual speed as a distance per unit time during the locomotion event controllably tracks the desired speed;

wherein outputting the stimulus frequency signal based on the error comprises determining a first control term proportional to the error which is used, at least in part, to determine the stimulus frequency signal; and wherein outputting the stimulus frequency signal based on the error comprises determining a third control term proportional to a time derivative of the error which is used, at least in part, to determine the stimulus frequency signal.

16. A method according to claim 15 wherein outputting the stimulus frequency signal based on the error comprises implementing a proportional-integral-derivative (PID) control scheme.

17. A method according to claim 16 wherein implementing the PID control scheme comprises generating a control signal based on the error and using the control signal as an input to a frequency generator which outputs the stimulus frequency signal in response to the control signal.

18. A method according to claim 15 wherein outputting the stimulus frequency signal based on the error comprises generating a control signal as a combination of available control terms and using the control signal as an input to a frequency generator which outputs the stimulus frequency signal in response to the control signal.

19. A method according to claim 18 comprising updating the control signal with a control period of less than 10 seconds.

20. A method according to claim 18 comprising updating the control signal with a control period of less than 1 second.

21. A method according to claim 18 wherein the stimulus frequency signal is provided to the subject in a form of music and the control signal is updated at a conclusion of each musical piece.

22. A method according to claim 15 wherein the stimulus frequency signal comprises an auditory signal that is output to the subject.

23. A method according to claim 15 wherein the stimulus frequency signal comprises one or more of: a tactile signal that is output to the subject and a visual signal that is output to the subject.

24. A method according to claim 15 wherein the desired speed comprises a user-specified speed profile.

25. A method according to claim 24 wherein the user-specified speed profile comprises an interval profile which comprises a plurality of intervals with each interval comprising at least one of: a desired speed level for a desired period of time; and a desired speed level for a desired distance.

26. A method according to claim 24 wherein the user-specified speed profile comprises a ramping speed profile which includes one or more time periods when the desired speed is increasing constantly with time.

27. A method according to claim 24 wherein the user-specified speed profile comprises a profile downloaded from a communication network.

28. A method according to claim 18 wherein the stimulus frequency signal is provided to the subject in a form of music and the control signal is updated at one or more intervals within a musical piece.

29. A method for guiding locomotion intensity in a human during a locomotion event, the method comprising:

estimating the subject's actual locomotion intensity during the locomotion event using one or more sensors to thereby obtain a measured intensity;

determining an intensity error during the locomotion event, the error comprising a difference between a desired intensity at a particular instant during the locomotion event and the measured intensity for the particular instant during the locomotion event; and if an absolute value of the intensity error is outside of a threshold region around the desired intensity during the locomotion event:

estimating the subject's actual locomotion speed as a distance per unit time at the particular instant during the locomotion event using one or more sensors to thereby obtain a measured speed as a distance per unit time for the particular instant during the locomotion event;

converting the desired intensity to a desired speed as a distance per unit time;

determining a speed error as a distance per unit time during the locomotion event, the error comprising a difference between the desired speed at the particular instant during the locomotion event and the measured speed for the particular instant during the locomotion event; and outputting, to the subject during the locomotion event, a speed-based stimulus frequency signal comprising a tempo wherein the tempo of the speed-based stimulus frequency signal is based on the speed error in such a manner that when the subject ambulates with a gait frequency that matches the tempo of the speed-based stimulus frequency signal, the subject's actual intensity during the locomotion event approximately controllably tracks the desired intensity; and if the absolute value of the intensity error is within the threshold region around the desired intensity during the locomotion event:

outputting, to the subject during the locomotion event, an intensity-based stimulus frequency signal comprising a tempo wherein the tempo of the intensity-based stimulus frequency signal is based on the intensity error in such a manner that when the subject ambulates with a gait frequency that matches the tempo of the intensity-based stimulus frequency signal, the subject's actual intensity during the locomotion event controllably tracks the desired intensity.

30. A method according to claim 29 wherein outputting the speed-based stimulus frequency signal based on the speed error comprises implementing a proportional-integral-derivative (PID) control scheme.

31. A method according to claim 30 wherein implementing the PID control scheme comprises generating a speed-based control signal based on the speed error and using the speed-based control signal as an input to a frequency generator which outputs the speed-based stimulus frequency signal in response to the speed-based control signal.

32. A method according to claim 31 wherein the speed-based stimulus frequency signal is provided to the subject in a form of music and the speed-based control signal is updated at one or more intervals within a musical piece.

33. A method according to claim 31 comprising updating the speed-based control signal with a speed-based control period of less than 10 seconds.

34. A method according to claim 31 comprising updating the speed-based control signal with a speed-based control period of less than 1 second.

35. A method according to claim 31 wherein the speed-based stimulus frequency signal is provided to the subject in a form of music and the speed-based control signal is updated at a conclusion of each musical piece.

36. A method according to claim 29 wherein outputting the intensity-based stimulus frequency signal based on the intensity error comprises implementing a proportional-integral-derivative (PID) control scheme.

37. A method according to claim 36 wherein implementing the PID control scheme comprises generating an intensity-based control signal based on the intensity error and using the intensity-based control signal as an input to a frequency generator which outputs the intensity-based stimulus frequency signal in response to the intensity-based control signal.

38. A method according to claim 37 wherein the intensity-based stimulus frequency signal is provided to the subject in a form of music and the intensity-based control signal is updated at one or more intervals within a musical piece.

39. A method according to claim 37 comprising updating the intensity-based control signal with an intensity-based control period of less than 10 seconds.

40. A method according to claim 37 comprising updating the intensity-based control signal with an intensity-based control period of less than 1 second.

41. A method according to claim 37 wherein the intensity-based stimulus frequency signal is provided to the subject in a form of music and the intensity-based control signal is updated at a conclusion of each musical piece.

42. A method according to claim 29 wherein the speed-based stimulus frequency signal and the intensity-based stimulus frequency signal comprise an auditory signal that is output to the subject.

43. A method according to claim 29 wherein the speed-based stimulus frequency signal and the intensity-based stimulus frequency signal comprise one or more of: a tactile signal that is output to the subject and a visual signal that is output to the subject.

44. A method according to claim 29 wherein the desired intensity comprises a user-specified intensity profile.

45. A method according to claim 44 wherein the user-specified intensity profile comprises an interval profile which comprises a plurality of intervals with each interval comprising at least one of: a desired intensity level for a desired period of time; and a desired intensity level for a desired distance.

46. A method according to claim 44 wherein the user-specified intensity profile comprises a ramping intensity profile which includes one or more time periods when the desired intensity is increasing constantly with time.

47. A method according to claim 44 wherein the user-specified intensity profile comprises a profile downloaded from a communication network.

48. A method according to claim 29 wherein the threshold region around the desired intensity is defined to comprise an absolute intensity range around the desired intensity.

49. A method according to claim 48 wherein the locomotion intensity is reflected by one or more intensity indicators which comprise a heart rate of the subject and the absolute intensity range comprise a desired heart rate±x, where x is a beat rate parameter.

50. A method according to claim 49 wherein the beat rate parameter x is user-configurable.

51. A method according to claim 29 wherein the threshold region around the desired intensity is defined to comprise a percentage intensity range around the desired intensity.

52. A method according to claim 51 wherein the locomotion intensity is reflected by one or more intensity indicators which comprise a heart rate of the subject and the absolute intensity range comprise a desired heart rate±x, where x is a percentage parameter.

53. A method according to claim 52 wherein the percentage parameter x is user-configurable.

54. A method according to claim 29 wherein converting the desired intensity to a desired speed comprises using a combination of a model which maps locomotion intensity to locomotion speed and subject specific calibration data.

55. A method according to claim 54 wherein the subject specific calibration data is used to reduce an experimentally determined error between predictions of the model and measured calibration data.

56. A method according to claim 55 wherein the experimentally determined error comprises a combination of experimentally determined errors associated with the model at different intensity levels.

57. A method according to claim 29 wherein converting the desired intensity to a desired speed comprises using experimentally determined subject specific calibration data that maps locomotion intensity to locomotion speed for the subject and for a plurality of discrete intensity levels.

58. A system for guiding a locomotion intensity of a human during a locomotion event, the system comprising:
one or more first sensors for sensing one or more corresponding parameters of the locomotion movement of the subject during the locomotion event and for generating therefrom a measured speed as a function of distance per unit time which represents an estimate of the subject's actual locomotion speed at a particular instant during the locomotion event as a function of distance per unit time;
one or more second sensors for sensing one or more corresponding parameters correlated with an intensity indicator of the subject during the locomotion event and for generating therefrom a measured intensity which represents an estimate of the subject's actual locomotion intensity at the particular instant during the locomotion event;
a controller configured to:
determine an intensity error during the locomotion event, the error comprising a difference between a desired intensity at the particular instant during the locomotion event and the measured intensity for the particular instant during the locomotion event; and
if an absolute value of the intensity error is outside of a threshold region around the desired intensity during the locomotion event:
convert the desired intensity to a desired speed as a distance per unit time;
determine a speed error as a distance per unit time during the locomotion event, the error comprising a difference between the desired speed at a particular instant during the locomotion event and the measured speed for the particular instant during the locomotion event; and
output, to the subject during the locomotion event, a speed-based stimulus frequency signal comprising a tempo wherein the tempo of the speed-based stimulus frequency signal is based on the speed error in such a manner that when the subject ambulates with a gait frequency that matches the tempo of the speed-based stimulus frequency signal, the subject's actual intensity during the locomotion event approximately controllably tracks the desired intensity; and
if the absolute value of the intensity error is within the threshold region around the desired intensity during the locomotion event:
output, to the subject, an intensity-based stimulus frequency signal comprising a tempo wherein the tempo of the intensity-based stimulus frequency signal is based on the intensity error in such a manner that when the subject ambulates with a gait frequency that matches the tempo of the intensity-based stimulus frequency signal, the subject's actual intensity during the locomotion event controllably tracks the desired intensity.

59. A system according to claim 58 wherein, as part of outputting the stimulus frequency signal based on the error, the controller is configured to implement a proportional-integral-derivative (PID) control scheme.

* * * * *